United States Patent [19]

Artzer

[11] Patent Number: 5,201,430
[45] Date of Patent: Apr. 13, 1993

[54] INSTRUMENT HOLDER

[75] Inventor: Craig S. Artzer, Sterling, Colo.

[73] Assignee: Advent Medico, Inc., Evergreen, Colo.

[21] Appl. No.: 821,328

[22] Filed: Jan. 13, 1992

Related U.S. Application Data

[63] Continuation of Ser. No. 622,326, Nov. 27, 1990, abandoned, which is a continuation of Ser. No. 355,977, May 23, 1989, abandoned.

[51] Int. Cl.$^5$ ................................................ A47F 7/00
[52] U.S. Cl. .................................... 211/70.6; 206/370
[58] Field of Search ................ 211/70.6, 70.7, 89, 211/120; 248/441.1, 450, 37.3, 37.6, 146, 153, 174, 175, 302, 309.1, 316.1, 316.5, 316.6, 316.7, 316.8; 206/370

[56] References Cited

U.S. PATENT DOCUMENTS

| | | | |
|---|---|---|---|
| 653,051 | 7/1900 | Woods | 211/65 |
| 2,080,805 | 5/1937 | Brey | 211/89 |
| 3,819,039 | 6/1974 | Erickson | 211/89 |
| 4,223,791 | 9/1980 | Taggart | 211/120 |

FOREIGN PATENT DOCUMENTS

| | | | |
|---|---|---|---|
| 99226 | 7/1964 | Denmark | 211/120 |
| 2504681 | 8/1976 | Fed. Rep. of Germany | 211/120 |
| 669750 | 10/1964 | Italy | 211/120 |
| 154519 | 5/1956 | Sweden | 211/89 |
| 187659 | 2/1937 | Switzerland | 248/37.3 |

Primary Examiner—Robert W. Gibson, Jr.
Attorney, Agent, or Firm—Beaton & Swanson

[57] ABSTRACT

An instrument organizer having an elongated body member having a base portion and an upper portion. The upper portion includes spaced-apart, upstanding, resiliently flexible support members defining spaced-apart vertical slots along the body member. A plurality of instruments (e.g., medical instruments) can be supported in the slots in an upright manner such that they can be easily grasped and removed from the device when needed. The resilient support members push against the opposite sides of each instrument to hold it in an upright manner and yet enable the instrument to be removed easily.

10 Claims, 1 Drawing Sheet

INSTRUMENT HOLDER

This is a continuation of copending application(s) Ser. No. 07/622,326 filed Nov. 27, 1990, now abandoned which is a continuation of Ser. No. 07/355,977 filed on May 23, 1989, now abandoned.

FIELD OF THE INVENTION

This invention relates to apparatus and techniques for organizing instruments and tools. More particularly, this invention relates to apparatus and techniques for supporting and organizing instruments (e.g., medical instruments) on a support surface such as a table in an operating room.

BACKGROUND OF THE INVENTION

A variety of instruments are used in the operating room. Such instruments are often placed on a table or Mayo stand and propped up with a rolled towel. Sometimes the instruments extend over the lip of the Mayo stand, and sometimes the instruments are simply laid flat on the stand. The types of instruments handled in this manner are varied and include, for example, hemostats, scissors, scalpels, forceps, etc.

This procedure, however, has several disadvantages. For example, the instruments are not supported in an upright manner. As a result, they often fall over and are therefore more difficult to identify and to grasp. Further, when the instruments are simply laying on the table they occupy more space than is desired.

Also, after instruments are used and are placed back on the table, there is no time to line up and try to support the instruments in an upright manner. Thus, when it is necessary to use any of such instruments again, it is necessary to locate the proper instrument on the table and try to grasp it. This can be difficult, cumbersome, and time-consuming. Also, after an instrument has once been used in the operation it will have blood or other body fluids on it. This can make the instrument more difficult to grasp when it is needed again in the operation.

The prior system of laying the instruments on a Mayo stand or table is cumbersome and inefficient. The instruments overlap each other and tend to fall over on their side. Consequently, the proper instruments are difficult to locate and grasp when needed. Although the use of a rolled cloth towel is helpful for propping up one end of instruments on a stand or table, most hospitals no longer use cloth towels because of the expense and need for laundering. Paper towels do not work for supporting instruments in an elevated manner because they do not have sufficient internal strength to support the weight of the instruments.

There has not heretofore been provided a convenient and effective holder for supporting instruments in the operating room which enables such instruments to be readily and easily grasped when needed.

SUMMARY OF THE PRESENT INVENTION

In accordance with the present invention there is provided an instrument organizer for supporting an instrument (such as a surgical instrument) so that it can be easily grasped. The instrument organizer comprises an elongated body member having a base portion and an upper portion.

The upper portion includes a plurality of spaced-apart, upstanding, resiliently flexible support members defining a plurality of spaced-apart vertical slots along the body member. Adjacent support members can be urged apart when an instrument is pressed downwardly into one of the slots. Adjacent support members are resiliently urged against the instrument to support it.

The organizer of the invention is conveniently positioned on a table or Mayo stand in the operating room and is adapted to be used for all types of instruments (e.g., hemostats of all sizes and styles, scissors, scalpels, forceps, clamps, needle holders, etc.). The organizer helps to keep the instruments separated and facilitates increased efficiency in the operating room. The organizer can be provided in various sizes and styles, as desired. For example, it may include a plurality of upstanding fingers or projections in close proximity to each other.

The instruments can be easily and readily placed into the organizer without having to locate or position an instrument in a specific slot. Rather, the instrument will automatically slip into an open slot on its own when it is pushed downwardly against the organizer.

Other advantages and variations of the instrument organizer will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
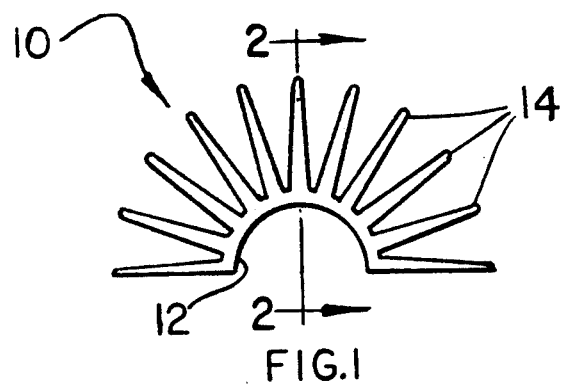
FIG. 1 is an end elevational view of one embodiment of instrument organizer of the invention.
Figure 2:
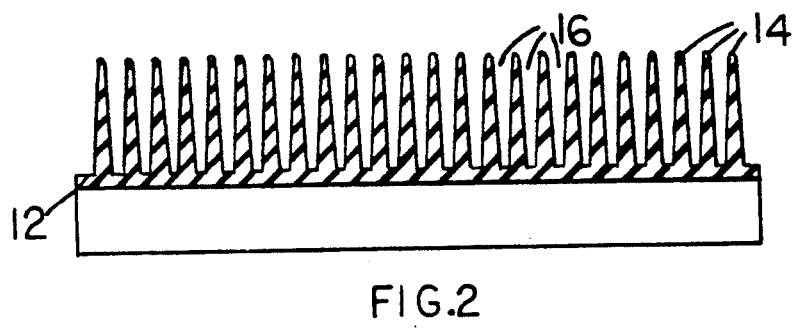
FIG. 2 is a cross-sectional view of the organizer shown in FIG. 1 taken along line 2—2.

In FIGS. 1 and 2 there is illustrated one embodiment of instrument organizer 10 of the invention for supporting an instrument (e.g., a surgical instrument) so that it can be easily grasped. The instrument includes an elongated body having a base portion 12 and an upper portion including a plurality of spaced-apart, upstanding, resiliently flexible support members 14. A plurality of spaced-apart vertical slots 16 are defined by the support members 14. Preferably the vertical slots are generally perpendicular to the longitudinal axis of the body member (or within about 10° of being perpendicular thereto).

In the embodiment shown in FIGS. 1 and 2 the support members are preferably made of plastic or rubber such that they can be deflected slightly to one side but they will try to resume their original position. As a result, when an instrument is forced into one of the slots between adjacent support members, the support members will be urged against the instrument and will support it in an upright manner. Yet, the instrument can be easily grasped and removed from the organizer when it is needed.

The length or height of the support members 14 in organizer 10 may vary. Generally speaking, it is preferred that they project upwardly from the base a distance of about 1.5 to 3 centimeters. The width of the vertical slots 16 (i.e., the distance between adjacent support members) may also vary (e.g., from about 0.1 to 1 centimeter, more preferably 0.2 to 0.6 centimeter).

The thickness of each support member 14 may also vary, so long as the support member is resiliently deflectable and is capable of supporting an instrument of its side in the manner illustrated herein. The support members may taper from their base to their outer ends, if desired. In the embodiment shown in FIGS. 1 and 2 the thickness of each support member at its lower end or base is about 0.25 centimeter and the thickness at its outer end is about 0.12 centimeter.

Figure 3:
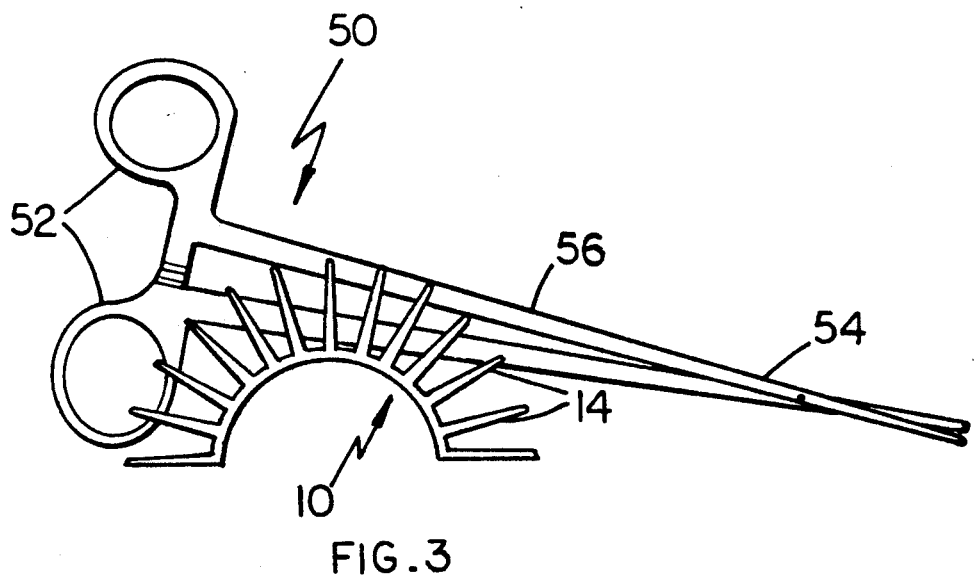
FIG. 3 is an end elevational view illustrating the embodiment of FIG. 1 being used to support a surgical instrument.
Figure 4:
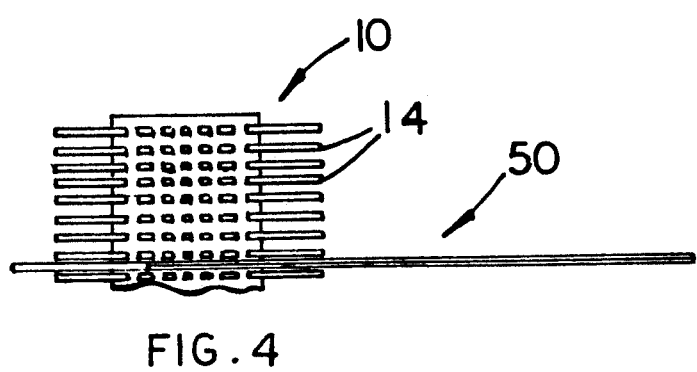
FIG. 4 is a top view showing the organizer and instrument shown in FIG. 3.

FIGS. 3 and 4 illustrate the use of the instrument organizer 10 of FIGS. 1 and 2 to support a hemostat 50 on its side in an upright manner so that it can be easily grasped when it is needed. As illustrated, the handles 52 of the hemostat may be easily grasped while the hemostat is in the organizer (or it may be grasped easily near its midpoint 56). The upright support members 14 prevent the hemostat from falling over to one side or the other. The forward end 54 (which is serrated) of the hemostat rests upon the table while the handle end is supported on the organizer. As will be readily appreciated from the drawings, many instruments may be supported in side-by-side manner in the organizer. The upright supports on opposite sides of each instrument prevent it from leaning over or falling over to either side.

The length of the instrument organizer of the invention may vary, as desired. Typically the length is in the range of about 6 to 20 inches, although it may be longer or shorter. The width of the organizer may also vary. Typically a width in the range of about 1 to 4 inches is sufficient.

It is preferred that the base portion of the organizer include a planar lower face or otherwise be capable of supporting the organizer in a stable manner on a table or other support surface. The base portion may have a width or length greater than the upper portion, if desired. The cross-sectional shape of the base portion may also vary (e.g., semi-circular, pyramid, square, rectangular, etc.).

It is also possible for the base portion to include fastening means thereon to facilitate fastening it to a table or support surface. For example, the base portion may include adhesive, or suction cups, or a hook-and-loop fastener (e.g., VELCRO brand fastener), or the like to temporarily secure or attach the organizer to a support surface.

The base portion may be composed of any of a variety of materials. Typically it is most economical to use a plastic or rubber material which can be easily extruded or molded. Other materials, of course, could also be used. The upright support members may be composed of plastic, rubber, stainless steel wire, etc.

The instrument organizer of the invention can be sterilized and packaged in a manner such that it can be stored in a conventional manner and then opened when it is needed to support surgical instruments. When the organizer is composed of stainless steel it may be resterilized and re-used as many times as desired. The organizers made of plastic or rubber are intended to be disposable. It is also possible for the organizers to be made of other materials so long as the upright support members have the desired resiliency for supporting the instruments in an upright manner.

The size of the instrument organizer may vary, as desired. For example, when the organizer is to be used for supporting large instruments, the organizer may be larger than when the organizer is intended to be used for supporting smaller instruments. Alternatively, the height of the upright support members could be shorter at one end of the organizer than at the other end so that various sizes of instruments can be supported in the organizer.

The instrument organizer is very effective in keeping multiple instruments in an upright manner and in a generally parallel condition so that they are readily accessed and are readily available for being grasped when needed. Preferably the organizer supports the handles of the instruments in a manner such that the instrument forms an angle of at least about 20° with respect to the table or other support surface. By keeping the instrument in an upright manner, the organizer prevents the instruments from laying against or on top of each other.

Because instruments can be placed into the organizer without even looking at it, the organizer is very efficient to use. When an instrument is pushed downwardly onto the organizer the upright support members are forced apart to enable the instrument to automatically locate an available slot to be received in.

Other variants are possible without departing from the scope of the present invention. For example, the instrument organizer can be used in a variety of applications besides operating rooms.

What is claimed is:

1. An instrument holder, comprising:
   (a) an elongated body member having a base portion and an upper portion, said elongated body member having an upraised cross section, and
   (b) a plurality of upward-standing, spaced apart, finger-like spikes disposed on the upper portion of the elongated body member; said spikes being oriented so that they are generally perpendicular to the longitudinal axis of the elongated body member, and being disposed in an array defining a plurality of rows, each row having at least two spikes, said rows of spikes defining a plurality of spaced apart slots, each slot oriented at approximately a right angle to the longitudinal axis of the elongated body member; and said spikes being resiliently flexible so that adjacent spikes are urged apart when an instrument is pressed downwardly into one of said slots, and are urged together and against said instrument to support it once the instrument is in place.

2. The instrument holder of claim 1, wherein the upraised cross section of the elongated body member is of sufficient height relative to a support surface on which the instrument holder is being supported so that when an instrument is placed in the instrument holder with one end of the instrument touching the support surface and the other end of the instrument being raised above the support surface by the upraised cross section of the elongated body member, the angle formed between the instrument and the support surface is at least about 20°, the upraised cross section being sufficiently high to create said angle.

3. The instrument holder of claim 2, wherein:
   (a) said spikes are of varying lengths, being shorter at a first segment of the instrument holder than at a second segment of the instrument holder for supporting varying sizes of instruments in the instrument holder; and
   (b) the rows of spikes are spaced apart from one another at varying distances, being closer together at a first segment of the instrument holder than at a second segment of the instrument holder for holding various sizes of instruments in the instrument holder.

4. The instrument holder of claim 3, wherein the base portion of the elongated body member further comprises fastening means for temporarily fastening the instrument holder to a support surface.

5. The instrument holder of claim 4, wherein said finger-like spikes project upwardly from the upper portion of the elongated body member a distance in the range of about 1.5 to 3.0 centimeters; the rows of spikes are spaced apart from one another a distance in the range of about 0.1 to 1.0 centimeters; the spikes taper from their base to their outward tip; the length of the elongated body member is in the range of about 6 to 20 inches; and the width of the elongated body member is in the range of about 1 to 4 inches.

6. A method of handling a plurality of surgical instruments comprising:
(a) placing said instruments onto an instrument holder, said instrument holder including an elongated body member having an upraised cross section, and a plurality of upward-standing, spaced apart, finger-like spikes disposed on the outside surface of the elongated body member, the spikes being disposed in an array defining a plurality of rows, the rows of spikes defining a plurality of spaced apart slots each slot oriented at approximately a right angle to the longitudinal axis of the elongated body member, the spikes being resiliently flexible so that adjacent spikes are urged apart when an instrument is pressed downwardly into one of said slots, and said adjacent spikes are urged together and against said instrument to support it once the instrument is in place, the several instruments being placed onto said instrument holder so that the instruments are oriented generally at right angles to the elongated body member of the instrument holder and on top of the outward tips of the spikes thereof, and
(b) pressing downwards on said instruments so that each instrument is automatically sorted into its own spaced apart slot, the instrument holder being adopted to sort such instruments simultaneously as the instruments are pressed downwards against the outward tips of said spikes, such action urging each instrument into its own slot, the instruments coming to rest in said slots, the instruments being generally parallel to one another, and each instrument being supported by the upraised cross sectional surface of said instrument holder so that each instrument is disposed at an angle, one end of said instrument being higher than the other end thereof.

7. The method of claim 6, further comprising:
(a) viewing the instruments within said instrument holder, the instrument holder being adapted to display the instruments, the instruments being disposed generally parallel to one another to facilitate viewing of said instruments,
(b) selecting a desired instrument for removal from the instrument holder, and
(c) removing the desired instrument from said instrument holder, the instrument holder being adapted to permit removal of instruments, one end of each instrument being disposed higher than the other end thereof to facilitate grasping of said instrument.

8. The method of claim 7, wherein said instrument holder is sterilized and aseptically packaged prior to use so that it can be stored in a conventional manner and then opened when needed to hold medical instruments.

9. The method of claim 8, further comprising: discarding said instrument holder when a medical procedure is concluded, the instrument holder being disposable.

10. The method of claim 6, wherein the act of placing the instruments on top of said instrument holder and the act of pressing downwards on said instruments are both performed without looking at the instrument holder.

* * * * *